(12) United States Patent
Dacus

(10) Patent No.: US 9,289,305 B2
(45) Date of Patent: Mar. 22, 2016

(54) TOTAL KNEE ARTHROPLASTY WITH SYMMETRIC FEMORAL IMPLANT HAVING DOUBLE Q-ANGLE TROCHLEAR GROOVE

(75) Inventor: Eric M. Dacus, Salt Lake City, UT (US)

(73) Assignee: Joint Development, LLC, Salt Lake City, UT (US)

( * ) Notice: Subject to any disclaimer, the term of this patent is extended or adjusted under 35 U.S.C. 154(b) by 0 days.

(21) Appl. No.: 13/544,654

(22) Filed: Jul. 9, 2012

(65) Prior Publication Data

US 2013/0035765 A1 Feb. 7, 2013

Related U.S. Application Data

(60) Provisional application No. 61/514,625, filed on Aug. 3, 2011.

(51) Int. Cl.
*A61F 2/38* (2006.01)
*A61F 2/30* (2006.01)

(52) U.S. Cl.
CPC .............. *A61F 2/3859* (2013.01); *A61F 2/3877* (2013.01); *A61F 2002/3021* (2013.01); *A61F 2002/30215* (2013.01); *A61F 2002/30255* (2013.01); *A61F 2002/30688* (2013.01); *A61F 2002/30822* (2013.01); *A61F 2002/30892* (2013.01)

(58) Field of Classification Search
CPC ...... A61F 2/3836; A61F 2/3859; A61F 2/3877; A61F 2002/30688
USPC ............ 623/20.14, 20.15, 20.18, 20.19, 20.2, 623/20.21, 20.28, 20.35
See application file for complete search history.

(56) References Cited

U.S. PATENT DOCUMENTS

| | | | | | |
|---|---|---|---|---|---|
| 4,353,135 | A | * | 10/1982 | Forte et al. | 623/20.2 |
| 4,944,756 | A | * | 7/1990 | Kenna | 623/20.19 |
| 5,330,532 | A | * | 7/1994 | Ranawat | 623/20.27 |
| 2008/0058947 | A1 | * | 3/2008 | Earl et al. | 623/20.35 |

* cited by examiner

*Primary Examiner* — Brian Dukert
(74) *Attorney, Agent, or Firm* — Lowry Blixseth LLP; Scott M. Lowry

(57) ABSTRACT

A total knee arthroplasty includes a symmetric femoral prosthesis for articulating with a tibial prosthesis in the left or right leg of a patient. The symmetric femoral prosthesis includes an anterior flange having a symmetric and upwardly diverging, generally V-shaped, double Q-angle trochlear groove formed in an anterior side thereof for accommodating natural Q-angle tracking of a natural or prosthetic patella when the symmetric femoral component is surgically implanted in either the left or right leg of a patient. In a preferred form, the double Q-angle trochlear groove is formed with an angle of + or − about 10°, for a total groove angle of about 20°.

6 Claims, 3 Drawing Sheets

TOTAL KNEE ARTHROPLASTY WITH SYMMETRIC FEMORAL IMPLANT HAVING DOUBLE Q-ANGLE TROCHLEAR GROOVE

BACKGROUND OF THE INVENTION

This invention relates generally to an improved total knee arthroplasty, including a symmetric femoral prosthesis adapted for implantation into either the left or right leg of a patient. More particularly, this symmetric femoral prosthesis has an anterior flange with an upwardly diverging anterior and symmetric or double Q-angle trochlear groove formed therein to accommodate natural tracking of a natural or prosthetic patella as the knee is moved normally between a substantially fully flexed and a substantially fully extending position.

Total knee arthroplasties are generally known in the art, wherein the articulating surfaces of the knee joint are replaced by a femoral component adapted for affixation onto the lower end of a resected patient femur, and a tibial component adapted for affixation onto the upper end of a resected tibia. In a typical design, a bearing insert constructed from a biocompatible and relatively high density plastic material such as a high density polyethylene or the like is fitted onto the tibial component and defines a pair of concave depressions for seated articulation of a matching pair of arched or convexly shaped condyles defined at the lower end of the femoral component. Such knee prostheses are used upon failure of the natural anatomical structures of a patient's knee joint, due to injury or disease.

A residual problem remains, however, involving tracking of the natural or a prosthetic patella (knee cap) against the knee prosthesis, typically an anterior surface of the femoral component. More particularly, the patella normally tracks through an upwardly diverging so-called Q-angle ranging from about 0° when the knee joint is fully flexed to a lateral or laterally outboard angle of about 10° when the knee joint is fully extended. In other words, flexion of the knee decreases the Q-angle, whereas extension of the leg increases the Q-angle; this phenomenon is believed to be due to internal rotation of the tibia. Clearly, the lateral direction for the patient's left knee joint is opposite to the lateral direction for the patient's right knee joint.

In the past, anatomical tracking of the patella against the prosthetic femoral component has generally entailed the use of different femoral components for the patient's left knee vs. the right knee, wherein each femoral component has a so-called trochlear groove extending from the lower to the upper margins of the femoral component at a specified constant-width angle (typically about 6-9° or 5-10° from a vertical direction) for correct patella tracking. However, such use of different left vs. right femoral components undesirably increases the total knee arthroplasty production cost. Attempts to provide a single femoral component having a wider constant width dimension suitable for correct patella tracking irrespective of the left vs. right knee joint of the patient have resulted in poor overall patella tracking and associated patient discomfort when implanted into a patient.

There exists, therefore, a significant need for further improvements in and to the femoral prosthesis or femoral component of a total knee arthroplasty wherein the improved femoral component accommodates accurate anatomical tracking of a natural or prosthetic patella irrespective of the specific left or right knee joint of the patient into which the prosthesis is implanted. The present invention fulfills these needs and provides further related advantages.

SUMMARY OF THE INVENTION

In accordance with the invention, a total knee arthroplasty including a symmetric femoral prosthesis for articulating with a tibial prosthesis in the left or right leg of a patient. The symmetric femoral prosthesis includes an anterior flange having an upwardly diverging and symmetric double Q-angle trochlear groove formed therein for accommodating natural Q-angle tracking of a natural or prosthetic patella when used in the left or right leg of a patient. In the preferred form, the upwardly diverging double Q-angle trochlear groove extends from a lower generally centered end upwardly with an angle of + or − about 10°, for a total angular width of about 20°.

In the preferred form, the symmetric femoral prosthesis or femoral component includes a pair of rounded or convex condyles of symmetric size and shape for articulating against a bearing insert supported by a tibial prosthesis or tibial component of the total knee arthroplasty. In one form, the bearing insert is constructed from a high density and generally biocompatible plastic material, such as polyethylene or the like, and is adapted for assembly as by snap-fitting with the tibial component. In use, the femoral condyles comprise medial and lateral articulating surfaces which bear against mating surfaces on the bearing insert during normal knee flexion and extension movements, in accordance with implantation into the left or right leg of a patient.

The symmetric femoral component further comprises the anterior flange having a symmetric and upwardly diverging, generally V-shaped anterior trochlear groove formed therein. This symmetric trochlear groove is formed with a double Q-angle extending from a groove apex generally at a lower anterior notch between the pair of femoral condyles and diverging upwardly laterally within the anterior face of the anterior flange with a widening or diverging angle relative to a substantially vertical centerline of + or − about 10°, for a total angular width of about 20°. Importantly, this symmetrically formed upwardly diverging and double Q-angle trochlear groove accommodates correct patella tracking along the anterior face of the anterior flange between about 0° and preferably about 9-10° in the course of natural knee joint movement between fully flexed and fully extended positions, for both the left and right legs of the patient.

The patella can comprise a natural patella, or alternately, may comprise a patellar prosthesis adapted for implantation with the other prosthetic components into to the left or right leg of the patient. When a patellar prosthesis is used, at least one and preferably multiple forwardly or anterior extending pegs such as three pegs are used for secure implantation into a resected forward or anterior portion of the patient's patella. The patellar prosthesis includes a symmetric posterior face which can be domed, sombrero-shaped, or the like.

Other features and advantages of the invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
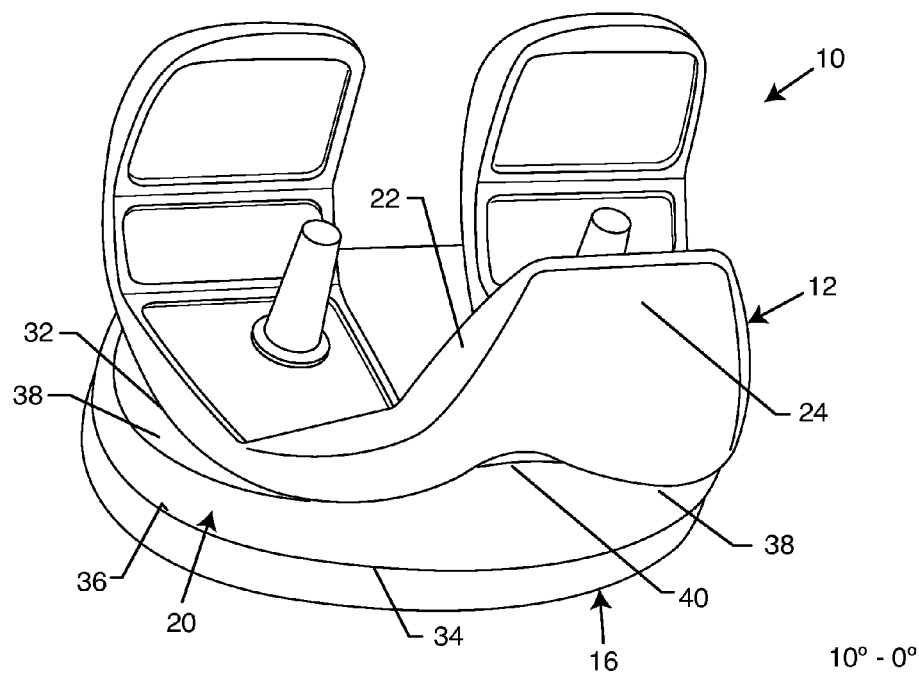
FIG. 1 is a top and anterior or front side perspective view of a total knee arthroplasty (TKA) constructed in accordance with the novel features of the invention, wherein a femoral component thereof includes an anterior flange having an anterior trochlear groove formed therein with an upwardly diverging and double Q-angle for accurate patella tracking irrespective of implantation of the TKA into the left or right knee joint of a patient.
Figure 2:
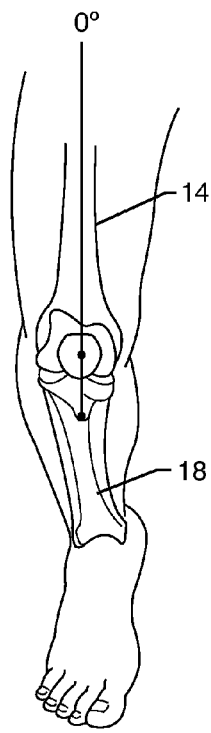
FIG. 2 is a fragmented front or anterior elevation view illustrating the Q-angle associated with patella tracking when the right knee joint of a patient is substantially fully flexed.
Figure 3:
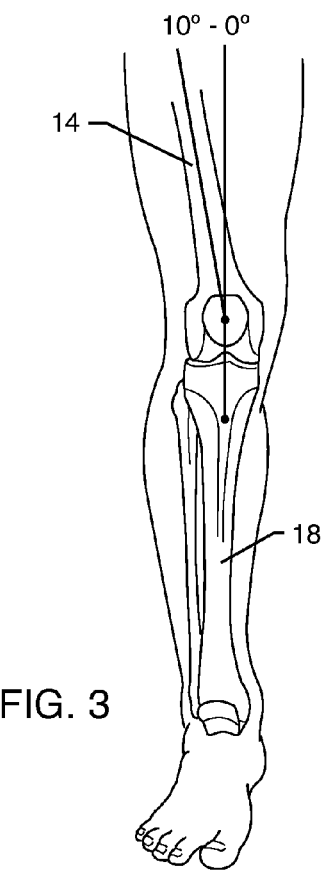
FIG. 3 is another fragmented anterior elevation view similar to FIG. 2 but showing the Q-angle associated with patella tracking when the right knee joint of the patient is substantially fully extended.
Figure 8:
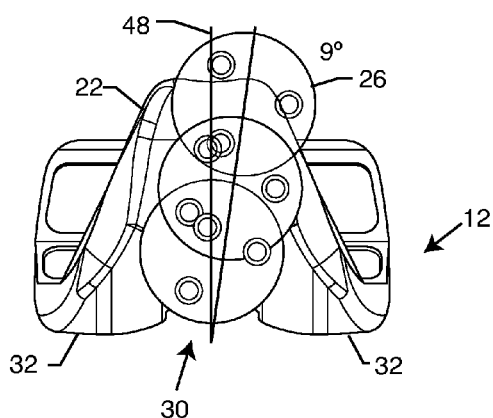
FIG. 8 is a composite anterior elevation view of the femoral component of FIG. 4 with a patella overlaid thereon in three different positions illustrating patella tracking between a fully flexed (0°) to a fully extended (about 9° lateral) of a patient's left knee joint.
Figure 7:
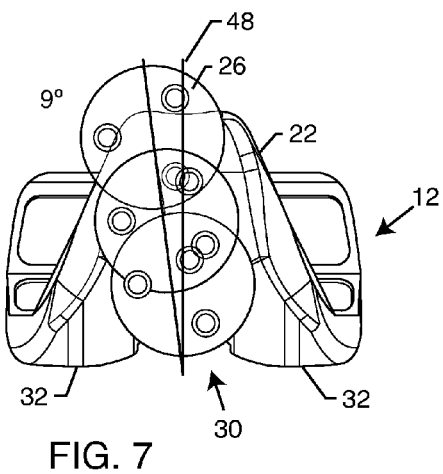
FIG. 7 is a composite anterior elevation view of the femoral component of FIG. 4 with a patella overlaid thereon in three different positions illustrating patella tracking between a fully flexed (0°) to a fully extended (about 9° lateral) of a patient's right knee joint.

As shown in the exemplary drawings, an improved total knee arthroplasty referred to generally in FIG. 1 by the reference numeral 10 is provided for implantation into a patient (not shown in FIG. 1). The knee arthroplasty or total knee prosthesis 10 comprises a femoral prosthesis or component 12 adapted for seated fit onto the lower end of a patient femur 14 (FIGS. 2-3), and a related tibial prosthesis or component 16 adapted for seated fit onto the upper end of a patient tibia 18 (FIGS. 2-3). A bearing insert 20 of high density plastic or the like is normally interposed between the femoral and tibial components 12, 16 for prosthesis articulation. In accordance with the invention, the femoral component 12 has a symmetric design suitable for implantation into either the left or right leg of a patient, with a forward or anterior flange 22 having formed therein at the forward or anterior side thereof having a double so-called Q-angle groove 24 for accommodating correct tracking of a natural patella or a patellar prosthesis 26 (FIGS. 7-8).

As shown generally in FIGS. 2-3, the so-called Q-angle associated with patella tracking changes in the natural knee joint as the knee is moved normally between a flexed position (FIG. 2) and an extended position (FIG. 3). More specifically, the so-called Q-angle of patella tracking is substantially 0° when the knee is fully flexed, but increases in the laterally outward direction relative to a vertical axis extending through the patient's femur 14 and tibia 18 to as much as about 10° in the fully extended position. FIGS. 2-3 illustrate this phenomena for the patient's right leg; it will be understood and appreciated that the Q-angle associated with patella tracking for the patient's left leg (not shown) will normally be in the opposite lateral direction by a substantially equal amount.

The femoral component 12 of the present invention has a generally symmetric design or shape suitable for implantation into either the left or right leg of the patient, with the femoral component 12 including the anterior wall or flange 22 having the double Q-angle trochlear groove 24 formed in the anterior side thereof to accommodate substantially normal tracking of a natural or prosthetic patella 26. In this regard, the double Q-angle groove 24 is shown best in FIGS. 4 and 5, having the general shape of an upwardly diverging "V", starting from a lower apex or point 28 at or near a central notch 30 formed between a pair of generally symmetric smooth-surfaced condyles 32. The double Q-angle groove extends upwardly with the general "V" configuration in the anterior side of the flange 22, to spread outwardly by about 10° in each direction from a vertical centerline, to a total angular width of about 20°. In use, when the knee prosthesis 10 is implanted into the right leg of a patient, the natural or prosthetic patella 26 is free to track normally along one side edge of the groove 24 between a lower flexed position of about 0° to an upper fully extended position of about 9-10° (FIG. 7). Similarly, when the knee prosthesis 10 is implanted into the left leg of a patient, the patella 26 is free to track normally along the opposite side edge of the groove 24 between a lower flexed position of about 0° to an upper fully extended position of about 9-10° (FIG. 8). With this construction, specialized femoral components suitable for unique implantation into the left or right leg only of a patient are avoided.

The knee prosthesis 10 of the present invention is surgically implanted into the patient, into either one of the left or right legs of the patient, substantially in a normal manner. That is, the femoral component 12 is adapted for implantation onto the lower end of a surgically resected patient femur 14, whereas the tibial component 16 is adapted for implantation onto the upper end of a surgically resected patient tibia 18. A suitable bone cement such as a polymethylmethacrylate (PMMA) is often used for affixing the femoral and tibial components 12, 16 to the respective patient bones, although persons skilled in the art will recognize and appreciate that one or more surfaces of the femoral and/or tibial components 12, 16 may be coated with a porous bone ingrowth coating (not shown) for ingrowth attachment to the adjacent patient bone. Both the femoral and tibial components 12, 16 are constructed in the preferred form from a strong metal or metal alloy, such as a titanium alloy or the like, having biocompatible properties.

The bearing insert 20 (FIG. 1) is normally provided between the upper femoral component 12 and the lower tibial component 16, wherein this bearing insert is normally constructed from a substantially biocompatible and relatively high density plastic material, such as a high density polyethylene or the like. This bearing insert 20 normally defines a substantially planar lower or underside surface 34 which is sized and shaped for secure support onto a substantially planar tibial platform 36 of the tibial component 16. The bearing insert 20 is normally secured onto the tibial platform 36 as by means of a snap-fit mounting (not shown) or the like. Alternative mounting arrangements such as one or more mounting screws are also known in the art.

An upper side or surface of the bearing insert 20 defines a generally concave pair of condylar surfaces 38 separated by a central ridge 40 extending generally anterior-posterior relative to the knee prosthesis 10. These concave condylar surfaces 38 are generally symmetric to each other, and are respectively adapted to receive and support the condyles 32 of substantially convex and mating shape on the lower end of the femoral component 12. Importantly, the notch 30 on the femoral component 12 between the convex condyles 32 extends generally anterior-posterior to accommodate condylar articulation substantially without interfering with the underlying ridge 40 on the bearing insert 20.

Figure 4:
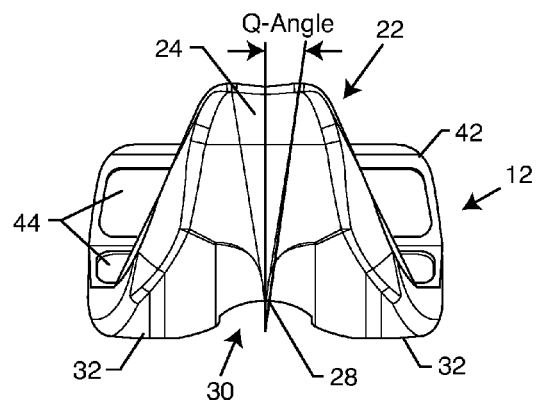
FIG. 4 is a front or anterior elevation view of the femoral component constructed in accordance with the invention to incorporate the anterior flange with the anterior trochlear groove formed therein with the upwardly diverging and double Q-angle for patella tracking when implanted into either the left or right knee joint of the patient.
Figure 5:
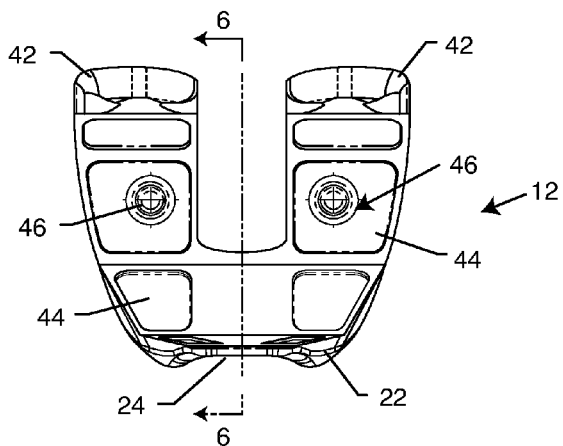
FIG. 5 is a top plan view of the femoral component of FIG. 4.
Figure 6:
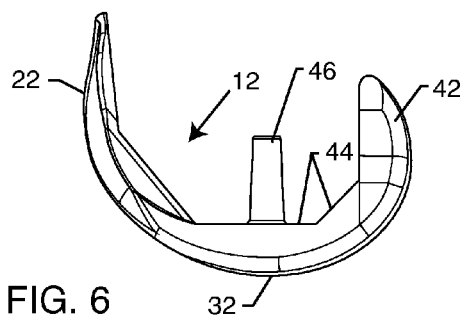
FIG. 6 is a vertical sectional view taken generally on the line 6-6 of FIG. 5.

FIGS. 4-6 illustrate the symmetric femoral component 12. As shown, the lower notch 30 defines the lower end or apex 28 of the double Q-angle groove 24 formed in an upstanding anterior wall or flange 22 thereof. A lower end of this anterior flange 22 is joined and blends smoothly with the medial and lateral convex lower condyles 32 of symmetric size and shape, wherein the medial and lateral character of the condyles 32 will vary according to the specific patient leg into which the knee prosthesis 10 is implanted. This pair of lower convex condyles 32 is physically separated or spaced from each other, with a posterior end thereof turning upwardly to define a short upstanding posterior wall or flange 42.

The upper or interior surfaces 44 of the femoral component 12 define areas of roughened texture for improved bonding by the selected bone cement to the resected patient bone. Alternately, as previously suggested, the areas 44 may incorporate a porous bone ingrowth structure for secure ingrowth attachment to patient bone. A pair of short posts 46 are shown upstanding from the upper or interior surfaces of the condyles 32 for press-fit or similar attachment into matingly shaped bores (not shown) formed in the resected patient bone.

FIGS. 7-8 depict normal tracking of the patella 26 when the femoral component 12 having the double Q-angle trochlear groove 24 formed therein is implanted respectively into the right leg (FIG. 7) or the left leg (FIG. 8) of the patient. Specifically, FIG. 7 shows the patella 26 tracking normally between a lower position of about 0° relative to a vertical centerline 48 when the knee joint of the right leg is substantially fully flexed, to an upper position displaced laterally outwardly along the groove 24 at an angle of about 9-10° (relative to the centerline 48) when the right leg is substantially fully extended. FIG. 7 also shows the patella 26 in an intermediate position part-way between the lower flexed position and the upper extended position.

FIG. 8 shows normal tracking of the patella 26 when the femoral component 12 is implanted into the left leg of a patient. The same vertical centerline 48 is shown in combination with the patella 26 being illustrated in the same three positions counterpart to FIG. 7. However, since the left leg of the patient is involved in FIG. 8, the patella 26 normally tracks along the opposite edge of the double Q-angle trochlear groove 24 as the patella shift is the now-opposite laterally outward direction between the lower flexed position and the upper extended leg position.

The symmetric femoral component 12 having the double Q-angle groove 24 of the present invention thus accommodates normal tracking of the patella 26, substantially without patient discomfort over a prolonged time period. The femoral component 12 can be used with a natural patella if the surgeon opts not to replace or to otherwise fit the natural patella with a prosthesis. However, the femoral component 12 also can be used with a patellar prosthesis in the event that the surgeon elects to use such patellar prosthesis with the total knee arthroplasty 10.

Figure 9:
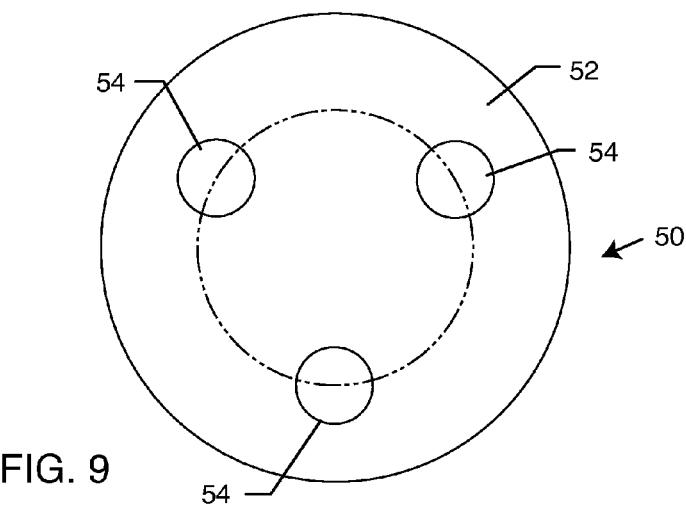
FIG. 9 is an anterior elevation view a domed patellar prosthesis for use in the TKA of FIGS. 1-8.
Figure 10:
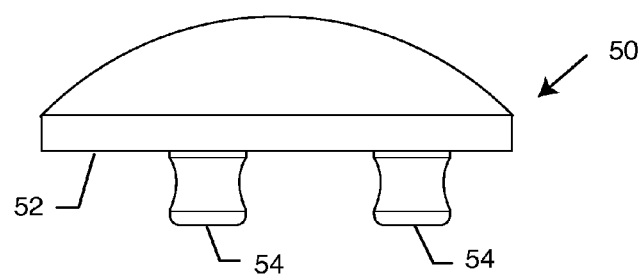
FIG. 10 is a top plan view of the domed patellar prosthesis of FIG. 9.
Figure 11:
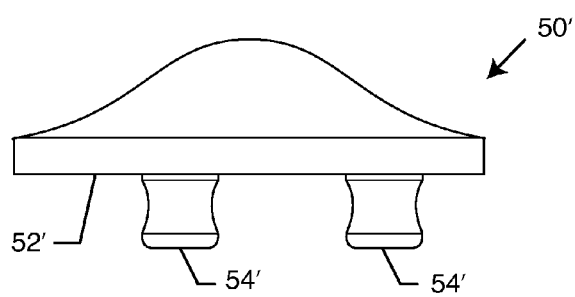
FIG. 11 is a top plan view similar to FIG. 10 but depicting an alternative sombrero-shaped patellar prosthesis for use in the TKA of FIGS. 1-8.

More particularly, as shown in FIGS. 9-10, a preferred patellar prosthesis 50 is shown wherein a posterior face 52 of the prosthesis 50 has a generally domed configuration adapted to translate smoothly and substantially without patient discomfort along the double Q-angle trochlear groove 24 (FIG. 4) of the symmetric femoral component 12. At least one and preferably multiple short contoured pegs 54 project forwardly or in an anterior direction from an anterior surface of the prosthesis 50 for suitable securement into matingly shaped opening or openings formed in natural patella bone which has been resected along a sagittal plane to remove a rear or posterior portion (not shown) thereof. FIG. 11 shows a similar patellar prosthesis 50', which is generally identical to the patellar prosthesis 50 shown in FIGS. 9-10, except that a posterior face 52' thereof is shaped with a generally sombrero profile. In either case, a preferred material used for these patellar prostheses 50, 50' comprises a biocompatible plastic material similar to that used for the bearing insert 20.

FIGS. 7-8 show the patella 26 tracking normally along the double Q-angle trochlear groove 24 in the anterior flange 22 of the femoral component 12, wherein this patella 26 may comprise one of the patellar prostheses 50, 50' of FIGS. 9-11. It will be recognized and understood, however, that the renderings of FIGS. 7-8 are equally applicable to a natural patella 26.

A variety of further modifications and improvements in and to the improved total knee arthroplasty including the symmetric femoral component of the present invention will be apparent to those persons skilled in the art. Accordingly, no limitation on the invention is intended by way of the foregoing description and accompanying drawings, except as set forth in the appended claims.

What is claimed is:

1. A knee prosthesis, comprising:
   a symmetric femoral component for implantation into the right or left leg of an arthroplasty patient at the lower end of a patient femur, said femoral component having a symmetric pair of generally convex condyles and an anterior flange;
   a generally symmetric trochlear groove converging proximally and formed within said anterior flange and having a double Q angle for tracking of a patient patella between a fully flexed leg position generally aligned with a central vertical axis of said trochlear groove and a fully extended leg position offset in a laterally outward direction from said vertical axis; and
   said femoral component having a geometry defining a continuous tangential transition between said anterior flange and said trochlear groove.

2. The total knee arthroplasty of claim 1 wherein said trochlear groove has a total angular dimension of about 20°.

3. The total knee arthroplasty of claim 1 wherein said double Q angle is upwardly diverging to accommodate relatively smooth tracking of the patient patella between an angle of about 0° when the knee is fully flexed to an angle of about 10° in a laterally outward direction when the knee is fully extended.

4. The total knee arthroplasty of claim 1 including a patellar prosthesis having a generally dome-shaped posterior face having a size and shape for tracking within said double Q angle trochlear groove.

5. The total knee arthroplasty of claim 4 wherein said patellar prosthesis has at least one contoured peg extending from an anterior surface thereof for attachment to an anterior portion of a natural patient patella.

6. The total knee arthroplasty of claim 1 wherein said trochlear groove generally converges proximally throughout the entire groove.

* * * * *